United States Patent
Berlich et al.

(10) Patent No.: US 12,337,092 B2
(45) Date of Patent: Jun. 24, 2025

(54) CONTAINER ARRANGEMENT, METHOD OF FILLING A CONTAINER ARRANGEMENT, AND USE OF A SOLUTION AS A DIALYSIS SOLUTION

(71) Applicant: Fresenius Medical Care Deutschland GmbH, Bad Homburg (DE)

(72) Inventors: Robert Berlich, St. Wendel (DE); Pascal Mathis, Saarwellingen (DE); Gerard Fu, Shanghai (CN); Richard Lasher, Knoxville, TN (US)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1087 days.

(21) Appl. No.: 17/273,371

(22) PCT Filed: Sep. 5, 2019

(86) PCT No.: PCT/EP2019/000256
§ 371 (c)(1),
(2) Date: Jan. 4, 2022

(87) PCT Pub. No.: WO2020/048628
PCT Pub. Date: Mar. 12, 2020

(65) Prior Publication Data
US 2022/0133972 A1 May 5, 2022

(30) Foreign Application Priority Data
Sep. 5, 2018 (DE) .................... 10 2018 121 675.0

(51) Int. Cl.
*A61M 1/28* (2006.01)
*A61J 1/10* (2006.01)
*A61J 1/14* (2023.01)

(52) U.S. Cl.
CPC ................ *A61M 1/287* (2013.01); *A61J 1/10* (2013.01); *A61J 1/1468* (2015.05); *A61M 2209/045* (2013.01)

(58) Field of Classification Search
CPC .. A61M 1/28; A61M 1/287; A61M 2209/045; A61M 1/167; A61J 1/10; A61J 1/1468
See application file for complete search history.

(56) References Cited

U.S. PATENT DOCUMENTS

| 2002/0091371 A1 | 7/2002 | Ritter |
| 2010/0016825 A1 | 1/2010 | Graf et al. |
| (Continued) | | |

FOREIGN PATENT DOCUMENTS

| CN | 101873871 A | 10/2010 |
| CN | 106516383 A | 3/2017 |
| (Continued) | | |

OTHER PUBLICATIONS

Office Action issued in corresponding Chinese Patent Application 201980058217.9 issued Apr. 18, 2024 (16 pages).

*Primary Examiner* — Susan S Su
*Assistant Examiner* — Erin A Kim
(74) *Attorney, Agent, or Firm* — Kilyk & Bowersox, P.L.L.C.

(57) ABSTRACT

The present invention relates to a container arrangement having a first container wherein the first container is either a container in which a concentrate is located that is configured to form a ready-to-use dialysis solution or a component thereof on a dilution with a solvent, preferably with pure water (water for injection), or an empty container, wherein the container arrangement has a second container in which the first container is received, with the first container having (Continued)

Figure 1:
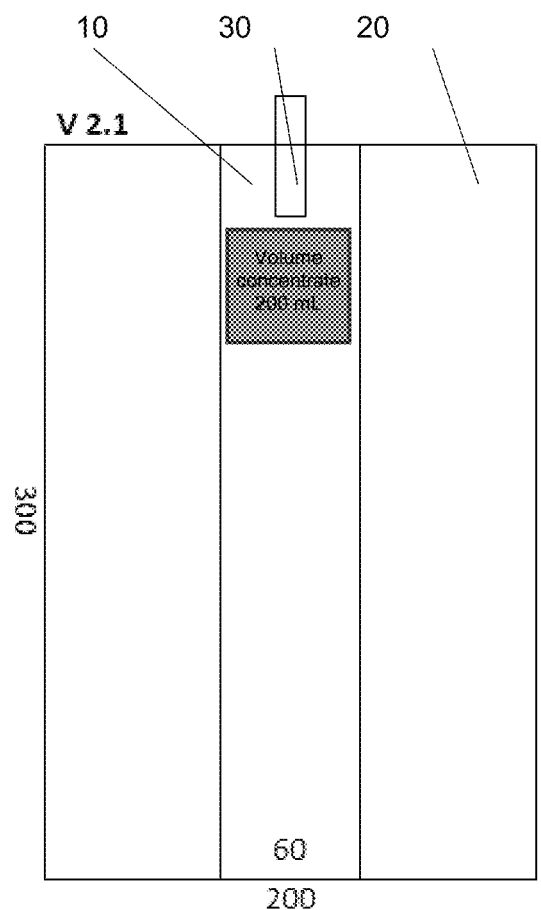

a greater elasticity than the second container and with the first container being configured to expand up to the second container.

17 Claims, 3 Drawing Sheets

(56) References Cited

U.S. PATENT DOCUMENTS

| | | | |
|---|---|---|---|
| 2010/0269909 A1 | 10/2010 | Brandl et al. | |
| 2012/0199532 A1* | 8/2012 | Eyrard | A61M 1/287 |
| | | | 206/223 |
| 2012/0310150 A1 | 12/2012 | Brandl et al. | |
| 2013/0281963 A1* | 10/2013 | Kugelmann | A61M 1/1666 |
| | | | 604/405 |

FOREIGN PATENT DOCUMENTS

| | | | |
|---|---|---|---|
| DE | 3726064 | 2/1989 | |
| DE | 19510759 | 10/1996 | |
| DE | 19510759 A1 * | 10/1996 | A61M 1/1637 |
| EP | 2484333 | 8/2012 | |
| EP | 2696910 | 2/2014 | |
| JP | 11-347314 A | 12/1999 | |
| JP | 2011235187 | 11/2011 | |

* cited by examiner

CONTAINER ARRANGEMENT, METHOD OF FILLING A CONTAINER ARRANGEMENT, AND USE OF A SOLUTION AS A DIALYSIS SOLUTION

The present invention relates to a container arrangement having a first container in which a concentrate is located that is configured to form a ready-to-use dialysis solution or a component thereof on a dilution with a solvent, preferably with pure water.

In addition to that, the present invention relates to such a container arrangement wherein the first container is empty. In this case, the first container is, for example, a drainage bag of a peritoneal dialysis system that is used to collect spent dialysis solution.

It is known from the prior art to use a sterile solution that includes water as the solvent, some physiological salts, buffers, and glucose for the dialysis treatment of a patient. The main component of the solution is water that makes up the main part of the solution by volume and by weight. Large quantities of ultrapure water are thus moved during the preparation process, the storage and the transport. This not only has disadvantages in handling and transport, but is also furthermore associated with the disadvantage that the transport and the storage bring along some energetic disadvantages.

It is the underlying object of the present invention to provide a container arrangement for the preparation of a dialysis solution that is simple to handle and to reduce the proportion of water that has to be moved during handling for the preparation of a dialysis solution. Further, it is an object of the present invention to provide an improved drainage bag for peritoneal dialysis.

This object is achieved by a container arrangement having the features of claim 1.

Provision is accordingly made that the container arrangement has a second container in which the first container is received, wherein the first container has a greater elasticity than the second container and wherein the first container is configured to expand up to the second container. The present invention is thus based on the idea of arranging a first container in a second container, wherein the first container is designed so elastically that it can expand up to the second container on a filling with a solvent, in particular with pure water (water for injection) or another liquid. Pure water is suitable for use in medical solutions, in particular for injection into the patient. Pure water is consequently typically sterilized.

The first container thus has the object of taking up the concentrate and the diluted, preferably ready-to-use, dialysis solution or a portion thereof and the second container has the object of giving the container arrangement structural strength and of bounding the expansion of the first container.

It is possible by the present invention to reduce the proportion of water and to provide a preferably liquid concentrate that is preferably appropriately packaged (stable, sterilizable by superheated steam, . . . ). It is preferred if this concentrate can be filled close to or at the patient's via a specific port only by the filling with ultrapure water for a ready-to-use solution.

The second container preferably does not come into contact with liquid and in this case does not have to satisfy any special properties with respect to the taking up of a liquid.

A separation or a distribution of the objects (taking up of liquid and structural strength) over the two containers is thus possible whose materials can thus be correspondingly selected.

It is, for example, conceivable that the second container is flexible, but not elastic. The case is also to be understood by "not elastic" that a very small elasticity is present. This is preferably so small that the second container bounds an expansion of the first container on its filling with a solvent.

The first bag is preferably flexible and elastic. The film of the first bag here preferably has an elongation at break of 400-900% in longitudinal and transverse directions.

To prevent an insulation effect due to an air cushion in the heat sterilization of the container arrangement, provision is preferably made that there is a vacuum between the first and second containers. The first container expands into this evacuated region on its filling, preferably until it contacts the first container. The air between the two bags can be removed very easily during preparation by welding/closing in the vacuum.

Provision is thus preferably made that the second container represents a bounding by volume in the expansion of the first container and provides the container arrangement with structural strength.

A particularly preferred embodiment results when the first container and/or the second container is/are a bag/bags.

The first and second containers can be directly or indirectly connected to one another at one or more points. An indirect connection is to be understood such that the first and second containers are fixed to a part of the container arrangement such as to a connector for filling and emptying the first container, but are not directly connected to one another.

A direct connection of the two containers at one or more points or side, e.g. by means of welding, is preferred.

A preferred connection of the containers is thus achieved by welding the containers.

It is conceivable that the first and second containers each have an upper end and a lower end and that the containers are connected, in particular welded, to one another at these two ends or at one of these ends. Other variants such as the welding of the bags only at one side, i.e. at the right side or at the left side, are also conceivable.

Provision can furthermore be made that the first container is provided with a connector that leads from the interior of the first container to the exterior. This connector or tube having a connector serves the filling of the first container with solvent or the emptying of the ready-to-use dialysis solution or a portion thereof from the expanded first container.

The second container preferably surrounds the first container completely.

The second container can represent the outer packaging of the first container. A function of the outer packaging is to set up a water vapor barrier. The film of the second container therefore preferably has a permeability of 0.2-5.0 g/(m$^2$*d) at 25° C. and at 40% relative humidity.

The concentrate is preferably present in liquid form in the first container. The use of a solid concentrate or the combination of a solid and a liquid concentrate is generally conceivable and covered by the invention.

It is further conceivable that the second container is partially or fully folded or rolled about the first container so that a space-saving container arrangement in particular results in storage and on transport.

The present invention relates to a method of filling a container arrangement in accordance with one of the claims 1 to 12 with solvent, in particular with pure water, wherein the solvent is filled into the first container that expands in this process. Instead of a solvent any other liquid can be used.

The filling is preferably carried out such that the first container expands up to the second container that represents a structural boundary of the expansion of the first container.

The invention further relates to the use of a solution prepared in accordance with a method in accordance with the invention as a ready-to-use dialysis solution, in particular as a peritoneal dialysis solution or as a component thereof.

A sufficient miscibility of the ingredients of typical dialysis solutions (glucose, salts, buffers) in the required concentration can be achieved with a tenfold (or greater) concentrated solution. The concentrate present in the first container is accordingly preferably concentrated ten times or more.

The concentrate preferably contains at least one osmotic agent and/or one or more electrolytes and/or one or more buffers and, particularly preferably, all the components required for the preparation of a dialysis solution except for the water required overall.

It has proved advantageous in practice, if the first container is a drainage bag of a peritoneal dialysis system.

In such an application, the second container preferably comprises a perforated and/or net-like structure, that forms a reliable support structure for the first container while requiring a minimum of material. For example, the second container can be configured as a bag formed of a net and/or can be made of strips, threads or cords. Using such a second container allows for manufacturing the first container with especially thin walls or from an especially elastic material, because the second container supports and protects the first container.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

In other words, the invention can be described as follows:

Aspect 1 of the invention relates to a container arrangement having a first container in which a concentrate is located that is configured to form a ready-to-use dialysis solution or a component thereof on a dilution with a solvent, preferably with pure water (water for injection), characterized in that the container arrangement has a second container in which the first container is received, with the first container having a greater elasticity than the second container and with the first container being configured to expand up to the second container.

Aspect 2 relates to a container arrangement in accordance with aspect 1, characterized in that the second container is flexible, but not elastic; and/or in that the first bag is flexible and elastic.

Aspect 3 relates to a container arrangement in accordance with aspect 1 or aspect 2, characterized in that there is a vacuum between the first and second containers.

Aspect 4 relates to a container arrangement in accordance with one of the preceding aspects, characterized in that the second container represents a boundary by volume on the expansion of the first container and gives the container arrangement structural strength.

Aspect 5 relates to a container arrangement in accordance with one of the preceding aspects, characterized in that the first and/or second containers is/are a bag/bags.

Aspect 6 relates to a container arrangement in accordance with one of the preceding aspects, characterized in that the first and second containers are directly or indirectly connected to one another at one or more points.

Aspect 7 relates to a container arrangement in accordance with aspect 6, characterized in that the connection takes place by welding.

Aspect 8 relates to a container arrangement in accordance with one of the preceding aspects, characterized in that the first and second containers have an upper end and a lower end; and in that the containers are connected, in particular welded, to one another at these two ends or at one of these ends.

Aspect 9 relates to a container arrangement in accordance with one of the preceding claims, characterized in that the first container is provided with a connector that leads from the interior of the first container to the exterior.

Aspect 10 relates to a container arrangement in accordance with one of the preceding aspects, characterized in that the second container represents the outer packaging of the first container.

Aspect 11 relates to a container arrangement in accordance with one of the preceding aspects, characterized in that the concentrate is present in liquid form.

Aspect 12 relates to a arrangement in accordance with one of the preceding aspects, characterized in that the second container is partly or fully folded or rolled around the first container.

Aspect 13 relates to a method of filling a container arrangement in accordance with one of the aspects 1 to 12 with solvent, in particular with pure water (water for injection), wherein the solvent is filled into the first container that expands in this process.

Aspect 14 relates to a method in accordance with aspect 13, characterized in that the filling is carried out such that the first container expands up to the second container that represents a structural boundary of the expansion of the first container.

Aspect 15 relates to a use of the solution prepared in accordance with a method in accordance with aspect 13 or aspect 14 as a ready-to-use dialysis solution, in particular as a peritoneal dialysis solution, or as a component thereof.

Further details and advantages of the invention will be explained in more detail with reference to an embodiment shown in the drawing.

Figure 2:
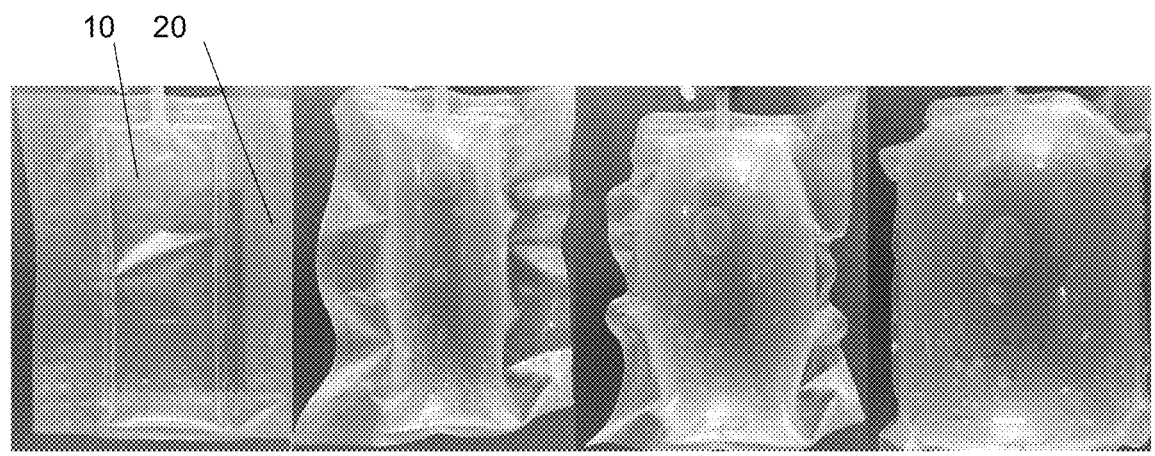
Figure 3:
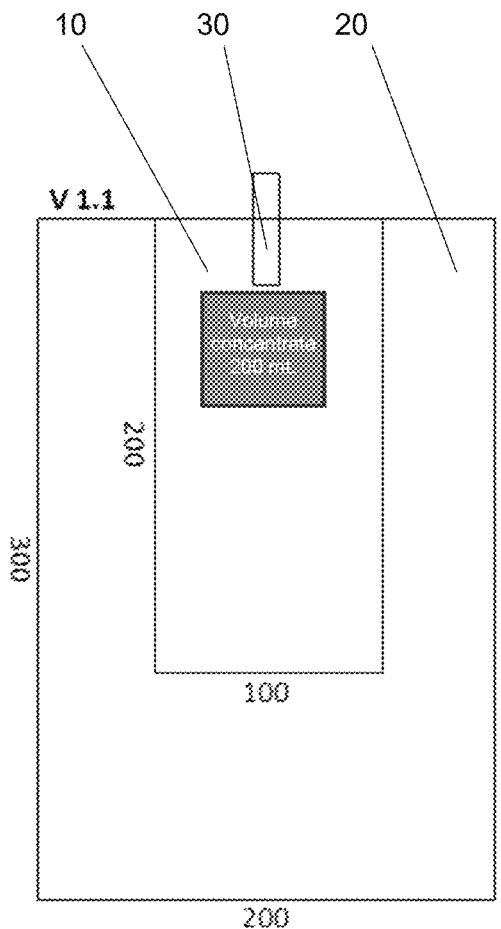
Figure 4:
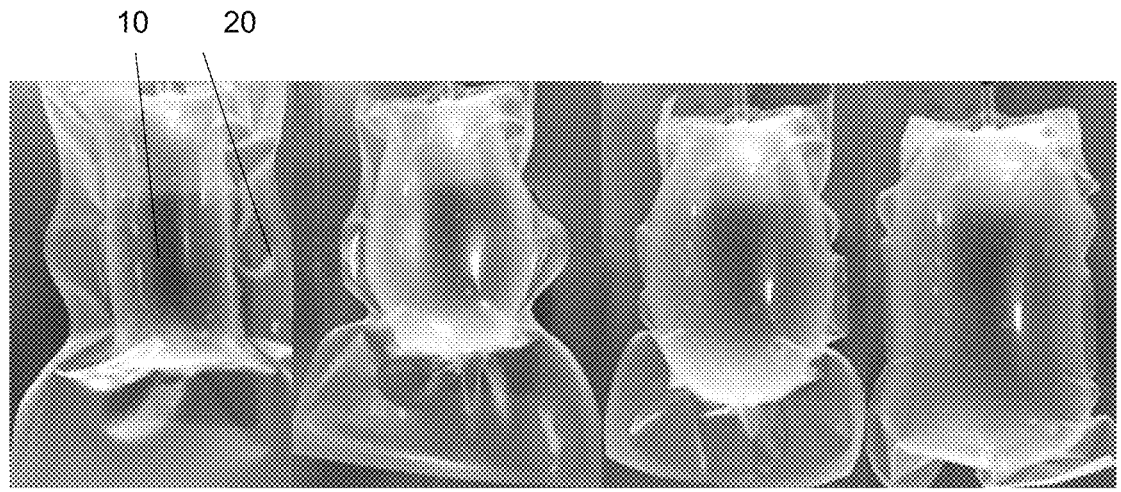

There are shown:

FIG. 1: a schematic view of a container arrangement in a first embodiment;

FIG. 2: views of the container arrangement in accordance with FIG. 1 in different stages of the filling of the first container with solvent;

FIG. 3: a schematic view of a container arrangement in a second embodiment; and FIG. 4: views of the container arrangement in accordance with FIG. 3 in different stages of the filling of the first container with solvent.

Figure 5:
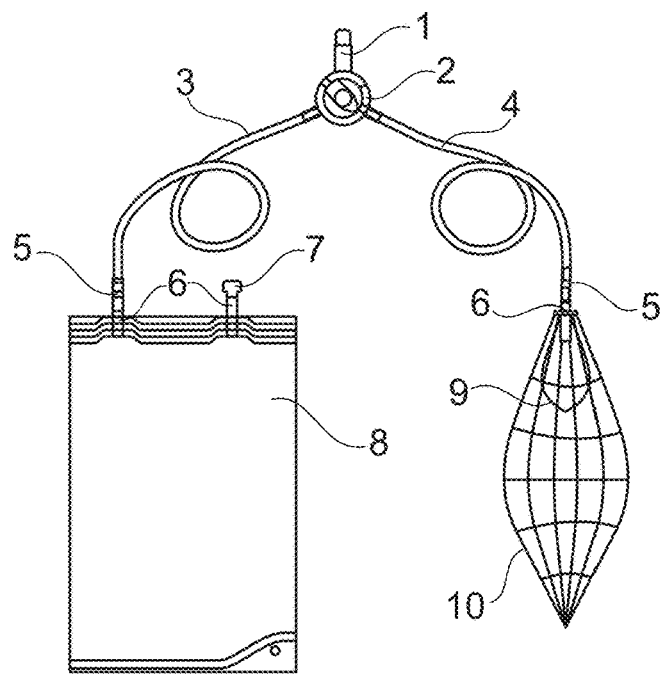
Figure 6:
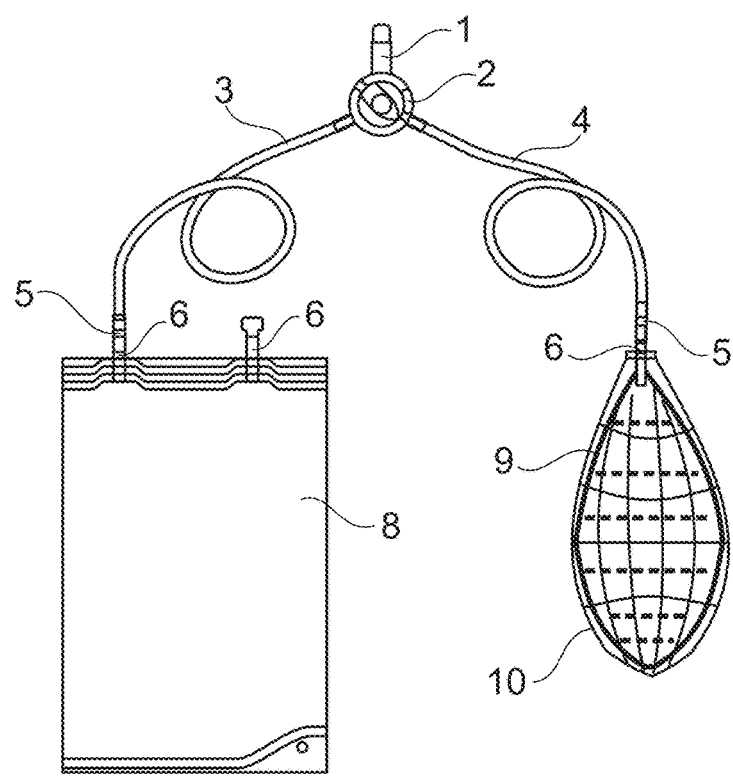

FIG. 5: a schematic view of a container arrangement in a third embodiment;

FIG. 6: a view of the embodiment of FIG. 5 in which the first container is filled.

An inner, small, and flexible bag that receives the concentrate is surrounded by a further bag that is larger than the inner flexible bag and that only represents an outer envelope for stabilization. This envelope can also simultaneously represent the secondary packaging.

In this case, a further smaller protective packaging may only be necessary at the connector. The flexible bag expands for the preparation of the ready-to-use solution, i.e. the first container expands into the larger outer bag, i.e. into the second container. There is here preferably no air between the inner bag and the outer bag, i.e. between the first and second containers. The removal of the air is to be preferred so that no insulation effect of the enclosed air occurs during superheated steam sterilization.

FIG. 1 shows by reference numeral 10 the first container in the form of the inner bag and by reference numeral 20 the second container that is likewise formed as a bag and represents the outer bag that surrounds the inner bag.

In accordance with FIG. 1, the inner bag 10 and the outer bag 20 are welded to one another at the upper end and at the lower end. The bag expansion of the inner bag takes place in a controlled manner here into both sides of the outer bag up to a complete filling such as can be seen from FIG. 2 that represents the filling at different points in time.

The inner bag 10 is provided with a connector 30 by means of which solvent or water can be filled into the inner bag 10 and the ready-to-use solution can be drained from the inner bag 10.

In the embodiment shown, the first container 10, i.e. the inner bag, has a volume of 200 ml and extends over the total height of the second bag that represents the outer packaging. This height amounts to 300 mm in the embodiment. The width of the first bag 10 amounts to 60 mm and the width of the second bag 20 amounts to 200 mm.

All of the aforesaid dimensions are not restrictive, but only exemplary and relate to the container arrangement before the filling of the first bag 10 with solvent, i.e. in the non-expanded state.

A bag arrangement is obtained by the filling with solvent that is preferably formed by pure water that adopts a volume of 2 l of ready-to-use solution.

In a further variant in accordance with FIG. 3, the inner bag 10 containing the liquid concentrate is only connected to the outer bag 20 at the upper side of said inner bag 10 (tube welding). The inner bag 10 admittedly hereby has to be pre-welded in a prior process step; however, a welding with the outer bag 20 can be omitted, which has advantages with respect to production technology.

In the embodiment shown in accordance with FIG. 3, the first container 10, i.e. the inner bag, has a volume of 200 ml and does not extend over the total height of the second bag that represents the outer packaging. The height of the first container 10 in the embodiment in accordance with FIG. 3 amounts to 200 mm and that of the second container 20 to 300 mm. The width of the first bag 10 amounts to 100 mm and the width of the second bag 20 amounts to 200 mm.

It also applies to this embodiment that all of the aforesaid dimensions are not restrictive, but only exemplary and relate to the container arrangement before the filling of the first bag 10 with solvent, i.e. in the non-expanded state.

A bag arrangement is obtained by the filling with solvent that is preferably formed by pure water that adopts a volume of 2 l of ready-to-use solution.

As can be seen from FIG. 4, on its filling with pure water, the first bag 10 expands at both sides and downwardly toward the second bag 20.

In general, the dimensioning of both bags and variants can be carried out such that different final volumes can be implemented.

The dimensions and the ratios of the dimensions of the two bags are based on the final volume and flexibility of the inner bag or of the first container.

In a preferred embodiment, the starting volume is at 0.1 liters-6.5 liters, preferably 0.2 liters-2 liters, particularly preferably 0.3 liters-1 liter, and the final volume is at 1 liter-65 liters, preferably 1.5 liters-12 liters, particularly preferably 2 liters-5 liters.

The empty overhanging parts of the outer bag, i.e. of the second container, can be folded or rolled around the bag for transport and storage. It is preferably ensured that a simple unfolding takes place during filling by expansion of the inner bag.

The material idea of the flexible inner bag 10, that can be transported in a protected manner in an outer bag 20 and that can later expand into it on filling, comprises the flexibility required for the function and the outer packaging/support effect being separated. A less expensive material selection can thereby take place. The flexible inner bag having a high proportion of expensive materials is much smaller in area and thus has a considerably lower consumption than the outer larger bag comprising less sophisticated and less expensive materials.

The following can be named as advantages of the present invention in a preferred embodiment:

Considerably less outer packaging or less outer packaging due to integration of a support function and protective function in one film; thereby less waste and cost savings.

Less storage and transport volume and lower weight. A better filling of tertiary packagings can thereby be achieved and less tertiary packaging is required, i.e. cardboard per solution bag.

Only a smaller solution bag 10 is required. A smaller surface-to-volume ratio thus results that promotes a small water loss and the advantage results that the filled solution bag can be overfilled because no or only briefer transport demands have to be satisfied or corresponding stiff support structures protect the bag.

In the embodiment shown in FIG. 5, the present invention is applied to a drainage bag of a peritoneal dialysis system. The drainage bag 9 is contained in a second container 10 that surrounds the drainage bag 9 like a net/a bag made of net. Drainage liquid/spent dialysis liquid can flow from a patient connector 2 after removal of a cap 1 and connection to a patient into the drainage bag 9 via a line 4, a connecting connector 5 and a connecting tube 6.

Via a line 3 fresh dialysis solution can be supplied to a patient from a container 8.

As shown in FIG. 6, the drainage bag 9 expands within the second container 10 when liquid, especially spent dialysis liquid, flows into the drainage bag 9.

The invention claimed is:

1. A container arrangement having a first container, wherein the first container is either a container in which a concentrate is located that is configured to form a ready-to-use dialysis solution or a component thereof on a dilution with a solvent, or an empty container, and the container arrangement has a second container in which the first container is received, with the first container having a greater elasticity than the second container and with the first container being configured to expand up to the second container, wherein there is a vacuum between the first and second containers.

2. The container arrangement in accordance with claim 1, wherein the second container is flexible, but not elastic; and/or in that the first bag is flexible and elastic.

3. The container arrangement in accordance with claim 1, wherein the second container represents a boundary by volume on the expansion of the first container and gives the container arrangement structural strength.

4. The container arrangement in accordance with claim 1, wherein the first and/or second containers is/are a bag/bags.

5. The container arrangement in accordance with claim 1, wherein the first and second containers are directly or indirectly connected to one another at one or more points.

6. The container arrangement in accordance with claim 5, wherein the connection takes place by welding.

7. The container arrangement in accordance with claim 1, wherein the first and second containers have an upper end and a lower end; and in that the containers are welded to one another at these two ends or at one of these ends.

8. The container arrangement in accordance with claim 1, wherein the first container is provided with a connector that leads from the interior of the first container to the exterior.

9. The container arrangement in accordance with claim 1, wherein the second container represents the outer packaging of the first container.

10. The container arrangement in accordance with claim 1, wherein the first container is a container in which a concentrate is located that is configured to form a ready-to-use dialysis solution or a component thereof on a dilution with a solvent, and the concentrate is present in liquid form.

11. The container arrangement in accordance with claim 1, wherein the second container is partly or fully folded or rolled around the first container.

12. A container arrangement having a first container, wherein the first container is either a container in which a concentrate is located that is configured to form a ready-to-use dialysis solution or a component thereof on a dilution with a solvent, or an empty container, and the container arrangement has a second container in which the first container is received, with the first container having a greater elasticity than the second container and with the first container being configured to expand up to the second container, wherein the first container is a drainage bag of a peritoneal dialysis system.

13. A container arrangement having a first container, wherein the first container is either a container in which a concentrate is located that is configured to form a ready-to-use dialysis solution or a component thereof on a dilution with a solvent, or an empty container, and the container arrangement has a second container in which the first container is received, with the first container having a greater elasticity than the second container and with the first container being configured to expand up to the second container, wherein the second container has a perforated and/or net-like structure.

14. A method of filling a container arrangement in accordance with claim 1 with liquid or solvent, wherein the liquid or solvent is filled into the first container that expands in this process.

15. The method in accordance with claim 14, wherein the filling is carried out such that the first container expands up to the second container that represents a structural boundary of the expansion of the first container.

16. A method of utilizing a solution comprising: filling the container arrangement in accordance with claim 1 with liquid or solvent to prepare the solution, wherein the liquid or solvent is filled into the first container that expands in this process; and using the solution as a ready-to-use dialysis solution or as a component thereof.

17. The container arrangement in accordance with claim 1, wherein the solvent is pure water.

\* \* \* \* \*